United States Patent
Abend

[11] Patent Number: 5,903,663
[45] Date of Patent: May 11, 1999

[54] AUTOMATIC ERROR RECOGNITION APPARATUS

[75] Inventor: Klaus Abend, Essingen, Germany

[73] Assignee: Tiede GmbH & Co.Risprüfanlagen, Essingen, Germany

[21] Appl. No.: 08/602,156

[22] Filed: Feb. 15, 1996

[30] Foreign Application Priority Data

Feb. 15, 1995 [DE] Germany .................. 195 05 064

[51] Int. Cl.$^6$ .................................................. G06K 9/00
[52] U.S. Cl. .................... 382/152; 382/154; 348/159
[58] Field of Search ................... 382/108, 141,
382/149, 152, 153, 154; 348/86, 92, 94,
95, 125, 128–130, 159, 47, 48; 356/237,
12; 364/468, 474, 5, 474.12; 250/558, 561–563;
219/121.64; 29/703, 709, 710; 395/119;
901/9, 16, 47

[56] References Cited

U.S. PATENT DOCUMENTS

| | | | |
|---|---|---|---|
| 4,146,924 | 3/1979 | Birk et al. | 382/153 |
| 4,207,593 | 6/1980 | Deutsch et al. | 348/134 |
| 4,835,450 | 5/1989 | Suzuki | 382/153 |
| 4,982,438 | 1/1991 | Usami et al. | 382/154 |
| 5,047,851 | 9/1991 | Sauerwein et al | 382/149 |
| 5,380,978 | 1/1995 | Pryor | 219/121.64 |
| 5,539,656 | 7/1996 | Annigeri et al. | 382/149 |

Primary Examiner—Christopher S. Kelley
Attorney, Agent, or Firm—Steinberg & Raskin, P.C.

[57] ABSTRACT

An apparatus and process for automatic error recognition for testing for tears in a magnetic-powder process during in-process control of image processing, whereby image recording units together with a downstream image processing unit evaluate areas with different optical characteristics from selected sample surface segments. In the process, a robot gasps at least one of the passing samples in precise position and brings the sample into a three-dimensional testing apparatus with image recording units arranged three-dimensionally, whereby the robot places the sample in precise position into the three-dimensional testing apparatus. The sample is then photographed by the image recording units which then transmit the obtained image information to a computer for evaluation. This computer is able to direct the robot accordingly based on its evaluation.

19 Claims, 1 Drawing Sheet

AUTOMATIC ERROR RECOGNITION APPARATUS

FIELD OF THE INVENTION

The present invention relates to an automatic error recognition apparatus and more particularly to an automatic error recognition apparatus for testing for tears using penetration media for in-process control of image processing, whereby image recording units together with a downstream image processing unit evaluate areas with different optical characteristics on selected sample surface segments.

The present invention also relates to a three-dimensional testing apparatus as well as a process for automatic error recognition in testing for tears according to the magnetic-powder process in in-process control for image processing, whereby image recording units together with a downstream image processing unit evaluate areas with different optical characteristics among selected sample surface segments, in particular according to the teachings of German Patent Publication No. DE 44 38 509.9.

BACKGROUND OF THE INVENTION

In testing work pieces with penetration media, such as powders capable of appearing fluorescent or also black powder or magnetic powder, i.e., conducting tests with a powder material for surface tears which thus highlighted upon examination under certain conditions and made more evident and detectable, CD cameras are used as the image recording units in automatic systems.

The CD camera, together with a downstream on-line computer, evaluates the magnetic powder data obtained from selected sample surface segments at a set algorithm.

The sample whose surface is normally evaluated for error indications for 100% with the human eye, is subdivided into segments for the evaluation of the automatic tear defect evaluation. The surface segments are selected for relevance of existing surface tears so that only the critical segments of the surface of the sample must be examined to ensure that they are free of tears. Otherwise, the examination of all of the surface of each sample would be unduly burdensome and time-consuming.

Generally, the number of the evaluated surface segments which are evaluated for tear indications determines the number of cameras.

The CD camera evaluates the tear indications with a luminosity threshold which assumes that all parameters relevant for an indication are kept as constant as possible with respect to luminosity. A parameter fluctuation resulting in luminosity changes causes a fluctuation of defect recognizability with the threshold of the camera.

Such systems have been described in publications, e.g., in German Patent Publication No. P 44 38 509.90 which is expressly referred to herein.

Conventional systems with a surface evaluation segment by segment are installed in large automobile component manufacturing plants for example. In these circumstances, a total of 18 interesting segments per part are selected from the total amount of surface segments. Each selected segment is examined with a camera for indications of tears in conjunction with the magnetic powder test.

The parts come out of production at a rate of about 18 seconds each. This means that every part must be evaluated for defects and must be conveyed into and out of the observation station within 18 seconds. This was achieved herein, as in all similar cases until now, in that 4 or 5 cameras evaluate the part in one station and in that the next 4 or 5 segments are evaluated in the next station, etc., i.e., by utilizing a plurality of examining stations. This means that the part to be examined is magnetized in an input station at a rate of one every 18 seconds and is then conveyed at the 18-second rate on a conveyor belt from the initial testing station with 4 cameras to the next, following testing station. At each testing station, 4 segments of the sample are the evaluated for indications of tears.

The cost of such a system is comparatively high, e.g., in view of the multitude of testing stations and number of cameras required in each testing station.

Furthermore, it is necessary to position the part to be examined on a pallet in such manner that all relevant surface segments can be covered by cameras. It is also necessary that the pallets be positioned in each testing station with a precision to within $\frac{1}{10}$th of a mm so that substantially the entire potential camera surface may be utilized. With each camera, the segment is set down so that on the surface on the one hand as many surfaces as possible can be evaluated, but on the other hand so that error messages, provoked by edges on the work piece may be ignored so that false interpretations may be avoided. This means that the less exact the positioning is, the smaller is the surface which can be used for surface indications after taking into account all tolerances.

In the above example, the weight of the parts to be tested (drag bearing) is approximately 15 kg. Thus, it is a disadvantage that the known pallets are expensive in construction, while a change in the pallet directly restricts the work piece surface which can be examined.

It is another disadvantage of this system that the pallets together with the work pieces to be tested must be transported by means of relatively expensive mechanical equipment from camera station to camera station.

There furthermore exists a system for the examination by the human eye in which the part is moved. The parts are currently examined on round tables on a rotating table top in the following manner. The work piece to be tested is introduced into the magnetizing station and is set on a receiving device on the table for that purpose. Following magnetization, the part, still lying in the receiving device, is conveyed to the observation point, is checked there and the sorting into good/bad (approved/rejected) is initiated. The receiving device present is then moved in steps to the unloading/reloading station and is conveyed from there again into the magnetizing station.

The same problems as for the first example apply, e.g., expensive construction of the parts involved in the system such as the tables.

OBJECTS AND SUMMARY OF THE INVENTION

It is therefore the object of the present invention to reduce the construction expenses of a testing system from those of a testing system according to the state of the art.

It is another object of the present invention to provide a new and improved automatic error recognition apparatus for testing for tears using penetration media for in-process control of image processing, whereby image recording units together with a downstream image processing unit evaluate areas with different optical characteristics on selected sample surface segments.

It is still another object of the present invention to provide a new and improved three-dimensional testing apparatus for testing for tears according to the magnetic-powder process in in-process control for image processing, whereby image recording units together with a downstream image processing unit evaluates areas with different optical characteristics among selected sample surface segments.

It is yet another object of the present invention to provide a new and improved process for automatic error recognition in testing for tears according to the magnetic-powder process in in-process control for image processing, whereby image recording units together with a downstream image processing unit evaluates areas with different optical characteristics among selected sample surface segments.

These objects and others are attained according to the invention by an automatic error-recognition apparatus comprising an automated robot which grasps passing samples in a precise position and a three-dimensional testing apparatus with three-dimensionally placed image recording units whereby the robot places the samples in precise position in the three-dimensional testing apparatus and removes them again from same. The image recording units transmit the received image information from the samples to a computer for evaluation and whereby the computer directs the robot accordingly. The computer may direct the robot to pass the samples to a reject area or spoilage, approved area or for further working, e.g., to correct defects.

Due to the fact that the parts to be tested are grasped by a robot, for example, in accordance with the invention, the robot may position the part in the magnetizing station and take charge of its transportation as described above, or may accept the part only after the magnetizing station. In this manner, the disadvantages of defect recognition apparatus utilizing linear transportation, in particular those occurring because the parts to be examined can be examined in at most three directions in linear transportation, are avoided.

In the invention, the part to be tested is positioned by means of the robot in front of a camera arrangement (or in a camera arrangement depending on the construction and configuration of the camera). In such a position, the cameras in the camera arrangement are able to scan the surface segments sequentially without further moving the part, so that no further mechanical movement is necessary, i.e., thereby avoiding the linear transportation prevalent in the prior art systems.

In an embodiment wherein ultraviolet illumination is needed to conduct the examination, the UV illumination needed for the evaluation can be obtained by means of UV flash lamps for optimal illumination of the surface segment being examined, as well as by means of a continuous UV light.

Following the sequential scanning of the surface by the cameras and the on-line evaluation of the individual camera indications, the robot can proceed with the sorting into good and bad (approved and rejected). It may however also place the tested work-piece in such manner in a marking device that a surface defect marking (spray pistol) takes place. With parts where rework (grinding) is necessary, it is also possible to position them automatically by means of the robot so that the marked locations can be ground.

In this manner, an additional saving is provided with such a device since parts sorted out as bad or rejected need no longer be transported in conveying containers to the rework machine to be conveyed there, in yet another step, to the grinding machine in a grinding-ready position.

It may be advantageous for the three-dimensional testing device to be provided with image recording units distributed three-dimensionally and a modular framework the individual parts of which can be assembled in function of the geometry of the parts to be tested. The modular framework can be designed to have any three-dimensional configuration including a plurality of stations in which samples are placed and cameras mounted to the framework for recording images of the samples.

It may also be advantageous to provide UV lamps in the testing apparatus to illuminate the material coated with magnetic powder capable of fluorescence to thereby cause the magnetic powder on the material to be fluorescent enabling easier viewing of tears in the material.

The automatic error recognition apparatus is advantageously provided with a marking device such as a spray pistol which marks the areas found to be defective.

It may also be advantageous for the error recognition apparatus to be provided with rework equipment supplied by the robot in which the sample can be reworked if necessary and re-evaluated if necessary, following the directions of the computer.

The present invention also relates to a testing apparatus with attachments distributed three-dimensionally for image recording units and, if applicable, lighting devices and with a modular framework, the individual modular components of which can be assembled in different ways as a function of the geometry of the part to be examined.

In addition, the present invention also relates to a process of the same type including a robot which is designed to grasp, in precise position, passing samples and in that the samples are brought into a three-dimensional testing apparatus with image recording units arranged in three dimensions, whereby the robot brings the samples in precise position into the three-dimensional testing device and removes them again from same, whereby the image recording units transmit the received image information to a computer for evaluation and the computer directs the robot accordingly.

It is advantageous for the robot to transfer the sample for rework or to place it back into production, depending on the directions received by the computer. To test the function of a testing apparatus which was modified by rebuilding the modular system, it is advantageous to use a calibration sample on which predetermined defects were created and by means of which the system can be adjusted at the beginning or can be checked at regular intervals. This is especially useful if the operator has effected modifications, whether intentionally or unintentionally, which were not supervised by specialized personnel.

Thus, in its most basic form, the automatic error recognition apparatus for detecting errors in an objects in accordance with the invention comprises a robot which holds the objects in precise, known positions, a three-dimensional testing apparatus including image recording units arranged to obtained images from the objects in three dimensions, whereby the robot transfers the objects into and from the testing apparatus such that when the objects are in the testing apparatus, the image recording units record images of selected segments of a surface of the objects, and image processing means, such as a computer, coupled to the image recording units for receiving the images of the selected surface segments from the image recording units and evaluating the images of the selected surface segments. The image processing means are coupled to the robot to control actions of the robot with respect to the transfer of the objects from the testing apparatus based on the evaluation of the images of the selected surface segments by the image processing means.

The testing apparatus may comprise a framework, in which case the image recording units are mounted in connection therewith. The framework comprises a plurality of discrete modular components assemblable in different configurations to provide a variety of testing configurations depending on the geometry of the objects. If the objects are coated with a magnetic powder capable of fluorescence, the testing apparatus may include ultraviolet lamps for illuminating magnetic powder in conjunction with the recordation of the images by the image recording means. A marking device may be included coupled to the image processing means for marking areas of the selected surface segments. A post-treatment device might be included coupled to the image processing means for reworking the objects in accordance with the evaluation of the images of the selected surface segments by the image processing means, whereby the robot is structured and arranged to transfer the objects to the post-treatment device.

The process for automatic error recognition in checking for tears in surfaces of objects comprises the steps of grasping in precise position each of the objects by means of a robot, conveying the objects into a three-dimensional testing apparatus, recording images of surface segments of the objects from three dimensions, processing the images of the objects to evaluate the presence or absence of tears in the surface segments, and controlling movement of the robot based on the evaluation of the presence or absence of tears in the surface segments. Also, the robot can be directed to transfer the objects with tears to a reworking station or to a production station. The object may be a calibration sample of the object with predetermined defects. The objects can be coated with a magnetic powder prior to the step of grasping the objects by means of the robot or after the step of grasping by the robot and prior to the step of conveying the objects into the testing apparatus.

The invention is explained in greater detail below through the drawing which shows a preferred embodiment of the apparatus according to the invention.

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1:
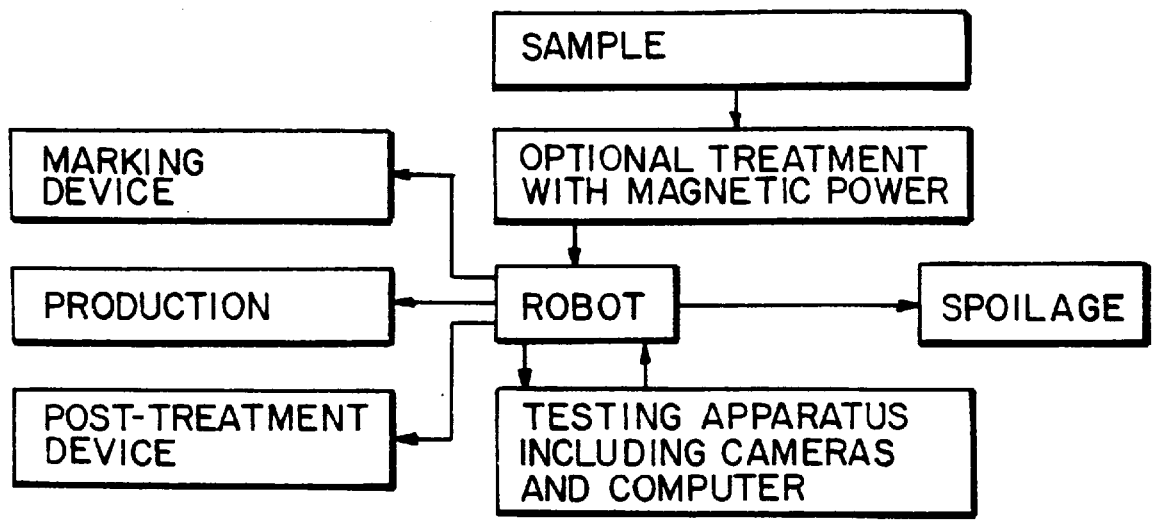
FIG. 1 shows a flow-chart of the apparatus according to the invention.
Figure 2:
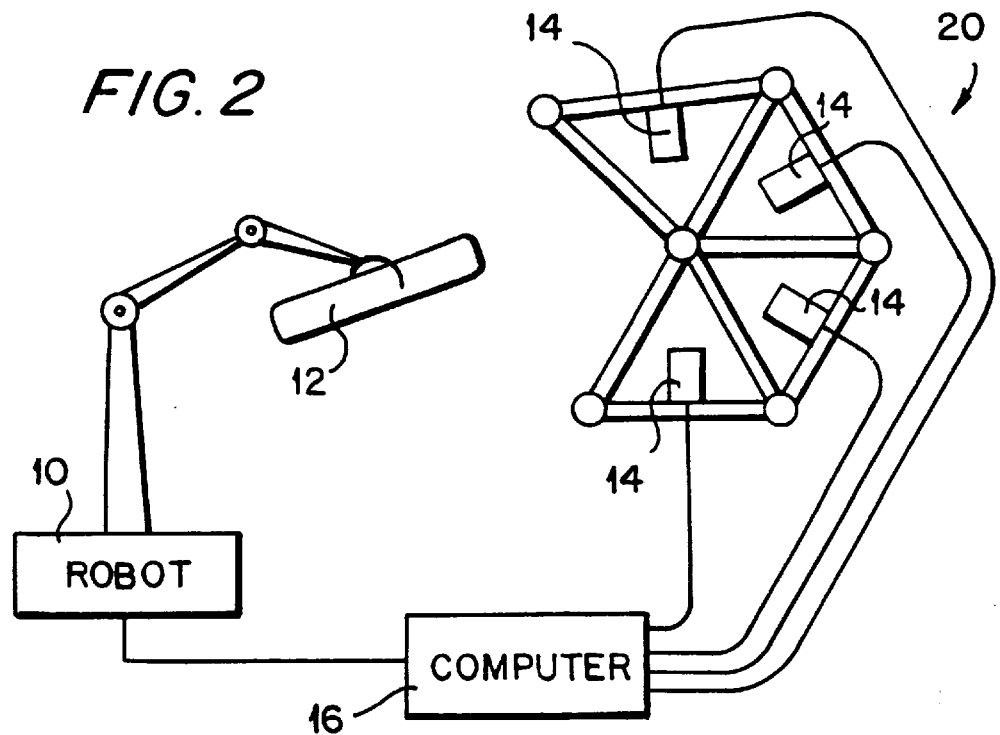
FIG. 2 is a schematic representation of an example of a testing apparatus in accordance with the invention.

Referring to the accompanying drawings wherein the same reference numerals refer to the same or similar elements, as shown in FIGS. 1 and 2, an object or sample 12 is coated in a known manner in a magnetic field with a test liquid containing magnetic particles with magnetic powder capable of fluorescence in solution or also in form of colored magnetic powder (so-called black powder). It is obvious though that other coatings can be applied to the sample 12 for the purposes of use in the testing apparatus in accordance with the invention without deviating from the scope of the invention.

The thus-coated sample is grasped by a robot 10 and is transferred into a three-dimensional testing apparatus 20. The sample 12 is photographed by image recording units such as a three-dimensional camera arrangement including at least one camera 14 in the testing apparatus 20. As shown in FIG. 2, the camera arrangement includes a plurality of cameras 14. Image processing means such as a computer 16 is coupled to the three-dimensional testing apparatus 20, and possibly directly to the three-dimensional camera arrangement 14, and evaluates values forwarded by the cameras 14 representatives of the images recorded by the cameras 14. Depending on the signal emitted by the computer 16 based on its evaluation of the received input from the camera(s) 14, the sample 12 can then be conveyed onward to be marked or to be reworked, being transported by the robot 10 to the location of further utilization. It is also envisioned that the sample 12 may be treated with the testing fluid after having been grasped by the robot, i.e., while it is already held by the robot arm.

FIG. 2 shows one possible embodiment of the three-dimensional testing apparatus 20 supplied by the robot 10 with samples 12. The robot 10 is constructed with appropriate members, e.g., arms, for grasping the sample 12 coated with magnetic powder in a precise position and holds it in the testing apparatus 20 so that it is photographed by the cameras 14 and is evaluated by the computer. As shown in FIG. 2, the cameras 14 are placed in specific positions in the testing apparatus 20 to take images of four sides of the samples 12, i.e., the cameras 14 may be positioned in different spatial coordinates whereby the height of the construction of each triangular module is different such that the computer receives images from the cameras of the samples taken in four different directions. The sides of the samples of which images are taken can be any sides in the three-dimensional coordinate system. Similarly, more cameras can be placed in connection with the modules in the testing apparatus to enable the testing apparatus to provide images from the cameras in numerous different directions.

In view of the fact that a practically three-dimensional camera arrangement is built up which can then be optimized for every sample or every work-piece geometry instead of the linear transportation, it is also possible to imagine so-called modular building sets in cuboid or spherical modules. A rod system for the positioning of the cameras and also possibly of the UV flash lamps can be provided in each cuboid. The seller or the buyer of a module can configure the camera arrangement anew, e.g., by assembling them or screwing them into place. In this connection, as shown in FIG. 2, the testing apparatus 20 includes elongate component parts joined at nodes by circular or spherical parts to formed a plurality of triangular or pyramidal modules. A respective one of the samples 12 is positioned by the arms of the robot 10 into each of the modules for observation. For a three-dimensional camera arrangement, the modules would constitute pyramidal modules formed by the joining of six elongate component parts at four nodes.

It is also possible to provide an aligning device or also a calibration sample through which the operation of the testing box may be checked and calibrated if necessary.

The examples provided above are not meant to be exclusive. Many other variations of the present invention would be obvious to those skilled in the art, and are contemplated to be within the scope of the appended claims. For example, although the invention is particularly directed to detecting tears, it is equally possible to detect other surface abnormalities in the objects being tested such as cracks, crevices and the like.

I claim:

1. An automatic error recognition apparatus for automatically detecting and evaluating cracks in unitary objects during in-process testing by image recognition, the unitary objects being coated with a magnetic powder capable of fluorescence or with black powder which accumulates in any unitary cracks of the objects, the system comprising:

a three-dimensional testing apparatus including image recording means for obtaining images of selected segments of a surface on at least two sides of the unitary objects, ultraviolet lamps for illuminating the unitary objects in conjunction with the recordation of the images by said image recording means such that in the images, any magnetic power or black powder accumulated in cracks in the unitary objects contrasts with the surfaces of the unitary objects, a robot for transferring the unitary objects into and from said testing apparatus such that when the unitary objects are in said testing apparatus, said robot holds the unitary objects in precise, preselected positions relative to said image recording means to enable said image recording means to obtain images of the selected surface segments on said at least two sides of the unitary objects, and image processing means coupled to said image recording means for receiving the images of the selected surface segments on said at least two sides of the unitary objects from said image recording means, said image processing means comprising a computer structured and arranged to evaluate the images of the selected surface segments for the presence of cracks in the selected surface segments to thereby detect any cracks in the selected surface segments, said image processing means being coupled to said robot to control actions of said robot with respect to the transfer of the unitary objects from said testing apparatus based on the evaluation of the images of the selected surface segments by said image processing means.

2. The apparatus of claim 1, wherein said testing apparatus comprises a three-dimensional framework, said image recording means being mounted in connection with said framework to obtain images of the selected surface segments on said at least two sides of the objects each from a different direction.

3. The apparatus of claim 2, wherein said framework comprises a plurality of discrete modular components, said modular components being assemblable in different configurations to provide a variety of testing configurations depending on the geometry of the objects.

4. The apparatus of claim 1, further comprising a marking device coupled to said image processing means for marking areas of the selected surface segments.

5. The apparatus of claim 1, further comprising a post-treatment device arranged at a different location than a location at which said testing apparatus is situated said post-treatment device being coupled to said image processing means for reworking the objects in accordance with the evaluation of the images of the selected surface segments by said image processing means.

6. The apparatus of claim 5, wherein said robot is structured and arranged to transfer the samples to said post-treatment device.

7. In an apparatus for testing for the presence of cracks in unitary objects including image recording means for recording an image of a surface of each unitary object and image processing means for evaluating the recorded images of the surface of the unitary objects to determine the presence of cracks in the surface of the unitary objects, the unitary objects being coated with a magnetic powder capable of fluorescence or with black powder which accumulates in any unitary cracks of the objects the improvement comprising:

a three-dimensional framework comprising a plurality of modular components forming a plurality of modules in which a respective one of the unitary objects is positionable, said modules being assembled in a specific pattern in accordance with the geometry of the unitary objects being tested, said image recording means being arranged on said framework to obtain and record images of surfaces on at least two sides of the unitary objects and said image processing means being structured and arranged to evaluate the presence of cracks in the surfaces on said at least two sides of the unitary objects and thereby detect any cracks in the surface of the unitary objects, and ultraviolet lamps for illuminating the unitary objects in conjunction with the recordation of the images of surfaces on at least two sides of the unitary objects by said image recording means such that in the images, any magnetic power or black powder accumulated in cracks in the unitary objects contrasts with the surfaces of the unitary objects.

8. The testing apparatus of claim 7, further comprising lighting means coupled to said modular components for illuminating the objects in said modules.

9. A process for automatic error recognition in checking for tears in surfaces of unitary objects, comprising the steps of:

grasping in precise position each of the unitary objects by means of a robot, conveying the unitary objects into a three-dimensional testing apparatus, coating the unitary objects with a magnetic powder such that the magnetic powder accumulates in any cracks in the unitary objects, recording images of surface segments on at least two sides of the unitary objects while the unitary objects are present in the testing apparatus, illuminating the unitary objects by means of ultraviolet lamps in conjunction with the recordation of the images of surface segments on at least two sides of the objects such that in the images, any magnetic power or black powder accumulated in cracks in the unitary objects contrasts with the surfaces of the unitary objects, processing the images of the unitary objects to evaluate the presence or absence of cracks in the surface segments on said at least two sides of the unitary objects, and controlling movement of the robot to transfer the unitary objects from the testing apparatus based on the evaluation of the presence or absence of cracks in the surface segments on said at least two sides of the unitary objects.

10. The process of claim 9, further comprising the step of directing the robot to transfer the objects with cracks to a reworking station.

11. The process of claim 9, further comprising the step of directing the robot to transfer the objects with cracks to a production station.

12. The process of claim 9, wherein the object is a calibration sample of the object with predetermined defects.

13. The process of claim 9, wherein the unitary objects are coated with the magnetic powder prior to the step of grasping the objects by means of the robot.

14. The process of claim 9, wherein the unitary objects are coated with the magnetic powder after the step of grasping by the robot and prior to the step of conveying the objects into the testing apparatus.

15. The apparatus of claim 1, wherein said image recording means comprise a plurality of cameras, each of said cameras providing an image of the surface on a respective side of the objects to thereby obtain images from all sides of the objects.

16. The apparatus of claim 1, wherein said image recording means comprise a plurality of cameras, each of said cameras being oriented toward the objects to provide an image of the object from a different direction.

17. The testing apparatus of claim 7, wherein said image recording means comprise a plurality of cameras, each of said cameras providing an image of a respective side of the objects to thereby obtain images from all sides of the objects.

18. The testing apparatus of claim 7, wherein said image recording means comprise a plurality of cameras, each of said cameras being oriented toward the objects to provide an image of the object from a different direction.

19. The process of claim 9, wherein said step of recording images comprises the step of positioning a plurality of cameras to provide an image of a respective side of the objects, and orienting the cameras toward the objects to provide an image of the object from a different direction.

* * * * *